US012805744B2

(12) United States Patent
Laviolette

(10) Patent No.: US 12,805,744 B2
(45) **Date of Patent: *Nov. 24, 2026**

(54) SYSTEMS AND METHODS FOR ESTIMATING HISTOLOGICAL FEATURES FROM MEDICAL IMAGES USING A TRAINED MODEL

(71) Applicant: The Medical College of Wisconsin, Inc., Milwaukee, WI (US)

(72) Inventor: Peter Sherman Laviolette, Wauwatosa, WI (US)

(73) Assignee: The Medical College of Wisconsin, Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/984,890

(22) Filed: Dec. 17, 2024

(65) Prior Publication Data

US 2025/0114010 A1 Apr. 10, 2025

Related U.S. Application Data

(63) Continuation of application No. 18/349,584, filed on Jul. 10, 2023, now Pat. No. 12,171,542, which is a (Continued)

(51) Int. Cl.
*A61B 5/055* (2006.01)
*G06N 20/00* (2019.01)
(Continued)

(52) U.S. Cl.
CPC ............. *A61B 5/055* (2013.01); *G06N 20/00* (2019.01); *G06T 7/0014* (2013.01); *G16H 30/40* (2018.01);
(Continued)

(58) Field of Classification Search
CPC ... A61B 5/055; A61B 2576/026; A61B 6/541; A61B 6/032; A61B 6/5217; A61B 6/501;
(Continued)

(56) References Cited

U.S. PATENT DOCUMENTS 6,009,342 A * 12/1999 Brasch ................. G01R 33/563 600/431
6,326,198 B1 12/2001 Emerson et al.
(Continued)

FOREIGN PATENT DOCUMENTS

CA 2717161 A1 6/2012
CA 2817161 A1 * 6/2012 ............. G01N 33/52
(Continued)

OTHER PUBLICATIONS

Kabli, Samira; He, Shuning; Herman P; Hurlstone, Adam; Jagalsk, Ewa Snaar; et al. In vivo magnetic resonance imaging to detect malignant melanoma in adult zebrafish. Zebrafish 7.2: 143(6). Mary Ann Liebert, Inc. (Jun. 2010) (Year: 2010).*
(Continued)

*Primary Examiner* — Linh Giang Le
(74) *Attorney, Agent, or Firm* — Quarles & Brady LLP

(57) ABSTRACT

Systems and methods for estimating quantitative histological features of a subject's tissue based on medical images of the subject are provided. For instance, quantitative histological features of a tissue are estimated by comparing medical images of the subject to a trained model that relates histological features to multiple different medical image contrast types, whether from one medical imaging modality or multiple different medical imaging modalities. In general, the trained model is generated based on medical images of ex vivo samples, in vitro samples, in vivo samples or combinations thereof, and is based on histological features extracted from those samples. A machine learning algorithm,
(Continued)

or other suitable learning algorithm, is used to generate the trained model. The trained model is not patient-specific and thus, once generated, can be applied to any number of different individual subjects.

7 Claims, 11 Drawing Sheets

Related U.S. Application Data continuation of application No. 17/510,055, filed on Oct. 25, 2021, now Pat. No. 11,696,701, which is a continuation of application No. 15/509,953, filed as application No. PCT/US2015/049656 on Sep. 11, 2015, now Pat. No. 11,154,212.

(60) Provisional application No. 62/049,011, filed on Sep. 11, 2014.

(51) Int. Cl.

| | |
|---|---|
| ***G06T 7/00*** | (2017.01) |
| ***G16H 30/40*** | (2018.01) |
| ***G16H 50/20*** | (2018.01) |
| ***G16H 50/50*** | (2018.01) |
| ***G16Z 99/00*** | (2019.01) |
| *A61B 6/00* | (2006.01) |
| *A61B 6/03* | (2006.01) |
| *A61B 6/50* | (2024.01) |

(52) U.S. Cl.
CPC ............. *G16H 50/20* (2018.01); *G16H 50/50* (2018.01); *G16Z 99/00* (2019.02); *A61B 6/032* (2013.01); *A61B 6/501* (2013.01); *A61B 6/5217* (2013.01); *A61B 6/541* (2013.01); *A61B 2576/026* (2013.01); *G06T 2207/20081* (2013.01); *G06T 2207/30096* (2013.01)

(58) Field of Classification Search
CPC ........ G16H 30/40; G16H 50/50; G16H 50/20; G06T 7/0014; G06T 2207/20081; G06T 2207/30096; G06F 19/00; G06N 20/00
See application file for complete search history.

(56) References Cited

U.S. PATENT DOCUMENTS

| | | | | |
|---|---|---|---|---|
| 7,761,240 | B2 * | 7/2010 | Saidi .................... | G06V 20/695 382/128 |
| 8,139,831 | B2 | 3/2012 | Khamene et al. | |
| 8,233,965 | B2 | 7/2012 | Bjornerud et al. | |
| 8,510,237 | B2 | 8/2013 | Cascaval et al. | |
| 9,404,986 | B2 | 8/2016 | White et al. | |
| 9,655,564 | B2 | 5/2017 | Sternickel et al. | |
| 2011/0044524 | A1 | 2/2011 | Wang et al. | |
| 2011/0075914 | A1 | 3/2011 | Filkins et al. | |
| 2012/0280686 | A1 | 11/2012 | White et al. | |

FOREIGN PATENT DOCUMENTS

| | | | |
|---|---|---|---|
| WO | 2002/025588 | A1 | 3/2002 |
| WO | 2009/058915 | A1 | 5/2009 |
| WO | 2013/028762 | A1 | 2/2013 |

OTHER PUBLICATIONS

The International Search Report and Written Opinion as mailed on Dec. 11, 2015 for International Application No. PCT/US2015/049656.

Bonekamp, D., et al. "Advancements in MR imaging of the prostate: from diagnosis to interventions." Radiographics 31.3 (2011): 677-703.

Chenevert TL, et al. Diffusion magnetic resonance imaging: an early surrogate marker of therapeutic efficacy in brain tumors. J Natl Cancer Inst. Dec. 20, 2000;92(24):2029-2036.

Donati OF, et al. Prostate Cancer Aggressiveness: Assessment with Whole-Lesion Histogram Analysis of the Apparent Diffusion Coefficient. Radiology. Dec. 12, 2013:130973.

Ellingson BM, et al. Graded functional diffusion map-defined characteristics of apparent diffusion coefficients predict overall survival in recurrent glioblastoma treated with bevacizumab. Neuro Oncol. Oct. 2011 ;13(10):1151-1161.

Ellingson BM, et al. Quantitative volumetric analysis of conventional MRI response in recurrent glioblastoma treated with bevacizumab. Neuro Oncol. Apr. 2011;13(4):401-9. Epub Feb. 15, 2011.

Ellingson BM, et al. Cell invasion, motility, and proliferation level estimate (CIMPLE) maps derived from serial diffusion MR images in recurrent glioblastoma treated with bevacizumab. J Neurooncol. Oct. 2011;105(1):91-101.

Ellingson BM, et al. Validation of functional diffusion maps (fDMs) as a biomarker for human glioma cellularity. J Magn Reson Imaging. Mar. 2010;31(3):538-548.

Ellingson BM, et al. Volumetric analysis of functional diffusion maps is a predictive imaging biomarker for cytotoxic and anti-angiogenic treatments in malignant gliomas. J Neurooncol. Aug. 27, 2011.

European Patent Office, Extended European Search Report for application 15839429.6, mailed on Mar. 28, 2018.

Franiel T, et al. Areas suspicious for prostate cancer: MR-guided biopsy in patients with at least one transrectal US-guided biopsy with a negative finding—multiparametric MR imaging for detection and biopsy planning. Radiology. Apr. 2011;259(1):162-172.

Futterer JJ, et al. Prostate cancer localization with dynamic contrast-enhanced MR imaging and proton MR spectroscopic imaging. Radiology. Nov. 2006;241(2):449-458.

Gauvain KM, et al. Evaluating pediatric brain tumor cellularity with diffusion-tensor imaging. AJR Am J Roentgenol. Aug. 2001;177(2):449-454.

Hambrock T, et al. Relationship between apparent diffusion coefficients at 3.0-T MR imaging and Gleason grade in peripheral zone prostate cancer. Radiology. May 2011;259(2):453-461.

Hayashida Y, et al. Diffusion-weighted imaging of metastatic brain tumors: comparison with histologic type and tumor cellularity. AJNR Am J Neuroradiol. Aug. 2006;27(7):1419-1425.

Hoeks CM, et al. Prostate cancer: multiparametric MR imaging for detection, localization, and staging. Radiology. Oct. 2011;261(1):46-66.

Hu LS, et al. Relative cerebral blood volume values to differentiate high-grade glioma recurrence from posttreatment radiation effect: direct correlation between image-guided tissue histopathology and localized dynamic susceptibility-weighted contrast-enhanced perfusion MR imaging measurements. AJNR Am J Neuroradiol. Mar. 2009;30(3):552-558.

Kinoshita M, et al. Fractional anisotropy and tumor cell density of the tumor core show positive correlation in diffusion tensor magnetic resonance imaging of malignant brain tumors. Neuroimage. Oct. 15, 2008;43(1):29-35.

Laviolette, P. S., et al. "Precise ex vivo histological validation of heightened cellularity and diffusion-restricted necrosis in regions of dark apparent diffusion coefficient in 7 cases of high-grade glioma." Neuro-oncology 16.12 (2014): 1599-1606.

Lyng H, et al. Measurement of cell density and necrotic fraction in human melanoma xenografts by diffusion weighted magnetic resonance imaging. Magn Reson Med. Jun. 2000;43(6):828-836.

Manenti G, et al. Malignant renal neoplasms: correlation between ADC values and cellularity in diffusion weighted magnetic resonance imaging at 3 T. Radiol Med. Mar. 2008;113(2):199-213.

Mickevicius et al, Brain Tumor Hypercellularity Detected in Diffusion Restricted Voxels Outside Contrast Enhancement in Six Human Brains Examined Ex-Vivo. ISMRM 2014 Milan, Italy.

Pope WB, et al. Recurrent glioblastoma multiforme: ADC histogram analysis predicts response to bevacizumab treatment. Radiology. Jul. 2009;252(1):182-189.

(56) References Cited

OTHER PUBLICATIONS

Sugahara T, et al. Usefulness of diffusion-weighted MRI with echo-planar technique in the evaluation of cellularity in gliomas. J Magn Reson Imaging. Jan. 1999;9(1):53-60.
Tanimoto A, et al. Prostate cancer screening: the clinical value of diffusion-weighted imaging and dynamic MR imaging in combination with T2-weighted imaging. J Magn Reson Imaging. Jan. 2007;25(1):146-152.
Laviolette, P.S. et al. "ADC-FLAIR Mismatch Excluding Enhancement (AFMEE), a Potential Biomarker of Tumor Infiltration" Society for Neuro-Oncology 2011 Annual Meeting.
Laviolette, P.S. et al. "Voxelwise Correlation of In-Vivo MRI to Ex-Vivo Brain Tumor Histology" Society for Neuro-Oncology 2011 Annual Meeting.
Kabli, S. et al., In Vivo Magnetic Resonance Imaging to Detect Malignant Melanoma in Adult Zebrafish, Zebrafish 7.2:143(6), Mary Ann Liebert, Inc. (Jun. 2010).

* cited by examiner

SYSTEMS AND METHODS FOR ESTIMATING HISTOLOGICAL FEATURES FROM MEDICAL IMAGES USING A TRAINED MODEL

CROSS-REFERENCE TO RELATED APPLICATIONS

This application is a continuation of U.S. patent application Ser. No. 18/349,584, filed Jul. 10, 2023, which is a continuation of U.S. patent application Ser. No. 17/510,055, filed Oct. 25, 2021, which is a continuation of U.S. patent application Ser. No. 15/509,953, filed Mar. 9, 2017, which represents the national stage entry of International Application No. PCT/US2015/049656, filed Sep. 11, 2015 which claims the benefit of and priority to U.S. Provisional Patent Application Ser. No. 62/049,011, filed on Sep. 11, 2014, and entitled "SYSTEMS AND METHODS FOR ESTIMATING HISTOLOGICAL FEATURES FROM MEDICAL IMAGES USING A TRAINED MODEL", which is incorporated herein by reference in its entirety.

BACKGROUND OF THE INVENTION

The field of the invention is systems and methods for medical imaging and histopathology. More particularly, the invention relates to systems and methods for estimating quantitative histological features from medical images of a subject using a trained model based on medical imaging and histology of tissue samples.

Understanding the histopathological basis underlying medical imaging is critical for optimal clinical interpretation. As one non-limiting example, many recent studies have concluded that current imaging technology is inadequate for detecting non-enhancing brain tumor based on the non-specific nature of current clinical imaging contrasts for this type of cancerous tissue.

Without voxel-wise histopathological validation, it is significantly difficult to interpret variations in imaging at the individual level. Current studies aimed at developing new imaging methods and biomarkers have been limited to population-level studies. In these studies, imaging is gathered on several patients and correlated with biopsy specimens. As an example, individual tumor heterogeneity, which is common in tumors, is lost in many analyses that use mean imaging values within regions-of-interest ("ROIs") to represent the tumor. Tumor heterogeneity, however, is a critical factor in designing individual therapies and understanding tumor status, as tumors are often stable in some regions and progressing in others.

There thus remains a need to understand and model individual tumor heterogeneity, and other tissue pathology states, histopathologically across many different imaging contrasts. It would therefore be desirable to provide systems and methods that are capable of providing a quantitative estimation of histological features based on different medical imaging contrasts, thereby providing systems and methods for non-invasive, in vivo histology of a subject.

SUMMARY OF THE INVENTION

The present invention overcomes the aforementioned drawbacks by providing a method for estimating quantitative histological features of a tissue using a medical imaging system. Image data is acquired from a subject using a medical imaging system, and a plurality of images of the subject are reconstructed from the acquired image data. A trained model that correlates a plurality of different medical image contrasts with histological feature data is provided, and quantitative histological feature values of a tissue in the subject are estimated by applying the trained model to the reconstructed images. In some embodiments, the trained model can be trained on images and histological data from the subject being imaged. In some other embodiments, the trained model can be trained on images and histological data not associated with the subject being imaged.

It is another aspect of the invention to provide a method for generating a trained model of quantitative histological features that are correlated with medical images. Image data is acquired from a subject with a medical imaging system, the image data representing a plurality of different image contrasts. A plurality of images of the subject are then reconstructed from the acquired image data. Quantitative histological features are acquired from a tissue sample obtained from the subject, and the trained model is generated by correlating the plurality of images of the subject with the acquired quantitative histological features using a machine learning algorithm.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for estimating quantitative information about histological features of a subject's tissue based on medical images of the subject. For instance, the systems and methods are capable of estimating quantitative histological features of a tissue by comparing medical images of the subject to a trained model that relates histological features to multiple different medical image contrast types, whether from one medical imaging modality or multiple different medical imaging modalities. In general, the trained model is generated based on medical images of ex vivo samples, in vitro samples, in vivo samples, or combinations thereof, and is based on histological features extracted from those samples, such as from microscopy images of those samples. A machine learning algorithm, or other suitable learning algorithm, is used to generate the trained model. The trained model is not patient-specific and thus, once generated, can be applied to any number of different individual subjects.

In general, the systems and methods described here provide the ability to understand and model individual tissue pathology states, such as tumor heterogeneity, histopathologically across multiple different imaging contrasts. This information can then be used to generate histological feature maps based on medical images of a subject. Rather than rely on medical image contrasts alone, the systems and methods described here combines medical image contrast information obtained from tissue samples with histological features measured in the same samples. Once this data is available, a training dataset can be generated and then applied to medical images collected from an arbitrary subject to generate histological feature maps of that subject. In this manner, the systems and methods of the present invention are capable of providing non-invasive, in vivo histological feature maps of a subject using only medical images of that subject and a pre-computed trained model.

The systems and methods described here are capable of quantifying, correlating, and generating machine learning algorithms for relating individual histological and histopathological features with multiple medical imaging contrast mechanisms on a voxel-wise basis. It is contemplated that these systems and methods will provide significant improvements for imaging and characterizing histopathological states of tissue in vivo by generating new comprehensive methods and training algorithms explicitly suited for correlating multiple medical image contrasts with different histological features of the underlying tissues.

Figure 1:
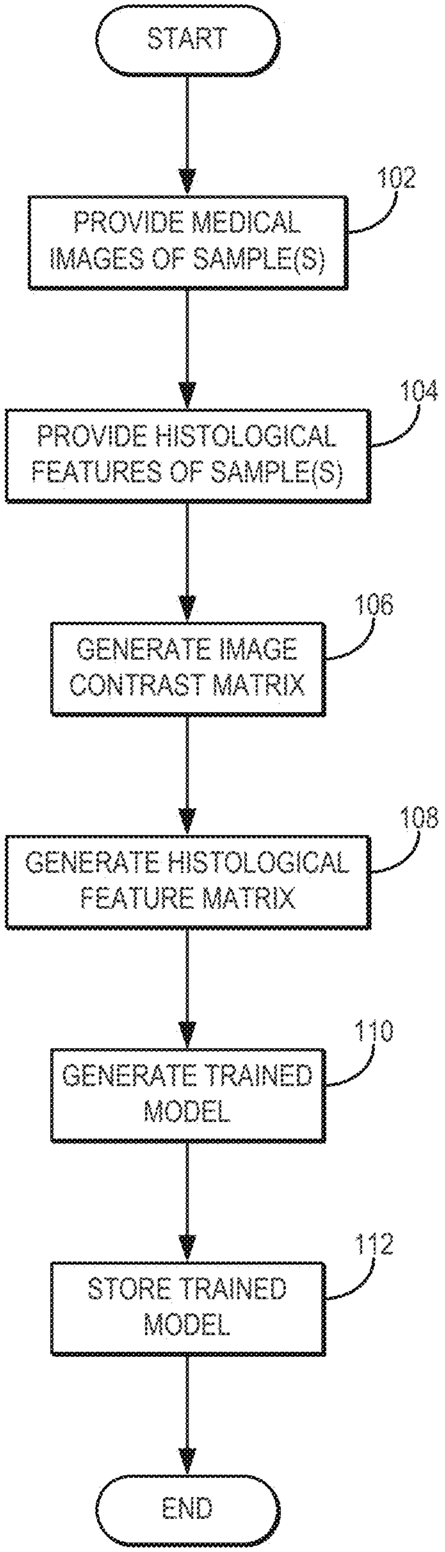
FIG. 1 is a flowchart setting forth the steps of an example method for generating a trained model that correlates multiple different medical image contrasts with quantitative histological features.

Referring now to FIG. 1, a flowchart is illustrated as setting forth the steps of an example method or generating a trained model that correlates medical image information to histological features. In general, the trained model may be generated based on information related to multiple different tissue samples, whether obtained in vivo or ex vivo.

The method includes providing one or more medical images of a plurality of different tissue samples, as indicated at step 102. The medical images of the tissue samples can be obtained using any suitable medical imaging system, including a magnetic resonance imaging ("MRI") system; an x-ray imaging system, including a computed tomography ("CT") system; an ultrasound imaging system; an optical imaging system; a nuclear medicine-based imaging system, such as a positron emission tomography ("PET") system; and so on.

Generally, the medical images will include multiple different images for the same two-dimensional image plane, or slice, of the sample, and may include multiple different images for each of a plurality of different image planes, or slices, through the sample. For instance, the provided medical images may includes multiple different magnetic resonance images obtained at each of a plurality of different slice locations using different image contrasts, such as $T_1$-weighting, $T_2$-weighting, diffusion-weighting, diffusion kurtosis imaging, and so on. The medical images may also include parametric images derived from or otherwise computed using the provided medical images. As one example, a parametric image may include an apparent diffusion coefficient ("ADC") map computed from diffusion-weighted magnetic resonance images. Other diffusion-based metrics can also be used, including those derived from diffusion tensor imaging, including mean diffusivity and fractional anisotropy. As another example, parametric maps of perfusion-based metrics, such as blood volume, blood flow, and mean transit time can also be used.

Figure 2:
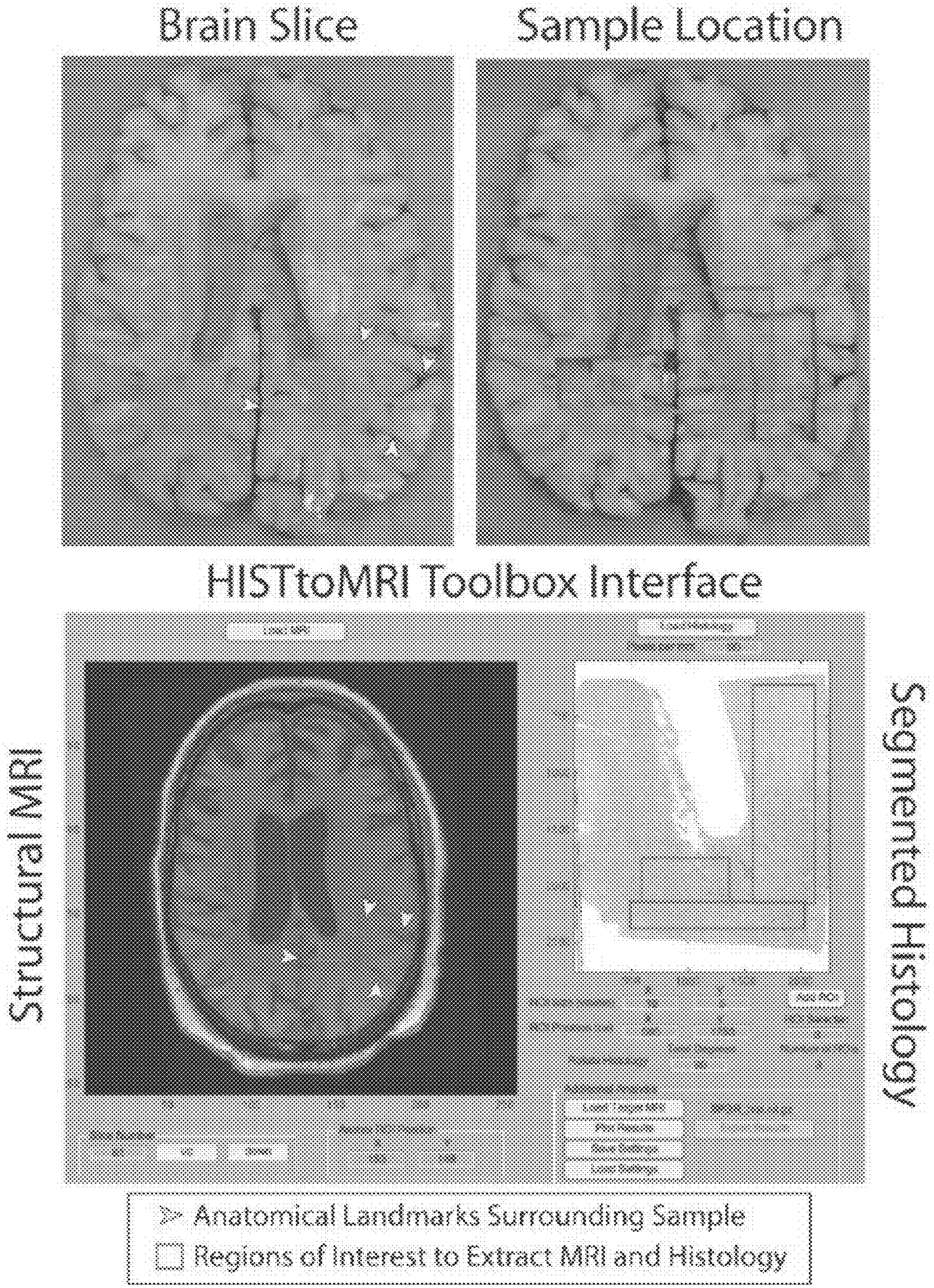
FIG. 2 is an illustrative example of a tissue sample and corresponding histology image and medical image of the tissue sample, wherein the histology image and the medical image are co-registered.

In some embodiments, the medical images of the tissue samples are acquired while the subject is still living, and the tissue samples are later resected for histological processing. In these instances, it is preferable to slice tissue samples in the same plane as the most recent medical images of the sample, and to slice the tissue sample as close as possible to the anatomical location represented in the medical images. An example of an MR slice closely matching a sliced whole brain sample is shown in FIG. 2, where anatomical landmarks (yellow arrows) in the photograph are visible in the corresponding MRI slice.

Referring again to FIG. 1, histological features of the plurality of tissue samples is also provided, as indicated at step 104. By way of example, the histological features can generally include quantitative information derived from histological samples, such as from digitized microscopy images of the samples. For example, the histological features can be associated with the size, shape, area, or number of cells, including separate measurements for different cell types. As one non-limiting example, the histological feature can be cell density, which is a measurement of the number of cells in a given volume of tissue. Advantageously, the histological feature can be attributable to particular cell types; thus, when analyzing an organ such as the prostate, separate maps can be generated to represent lumen density and gland wall density. As another example, the histological features can include cell or nuclei area; cell or nuclei stain heterogeneity; or cell or nuclei tortuosity. As still another example, the histological feature can be voxel-wise percentage of necrosis or vascularity. The histological features can also be associated with information derived from histology, such as tumor grade. For prostate tissues, the histological feature can thus include a Gleason score.

The histological features can also include quantitative information derived from staining. For instance, the histological features can be associated with the presence of different colors in a sample, the area of a given color in a sample, the relative proportions of different colors in a sample, or the intensity of one or more colors in a sample. When the stain is a fluorescent molecule, the histological feature may include quantifiable information derived from fluorescent imaging of the histological sample, such as fluorescence intensity. As an example, the histological feature can be any characteristic that can be quantified or labeled from histology using a microscope or other tool for evaluating tissue slides.

One example of how histological features can be obtained is now described. Tissue samples that have been previously images can be stained. As one example, the samples can be stained using an H&E stain. Each tissue slide can then be photographed across the entire sample. For instance, a motorized microscope stage can be used to obtain photographs of the stained slides. Each photograph can then be processed individually and stitched together to form a histology image of the tissue sample.

Additional processing can be performed on the histology image as necessary or desired. For example, to obtain a cell density measurement, thresholds for segmentation of cell nuclei can be applied and, following segmentation, the nuclei in each histology image can be counted to obtain a voxel-wise measurement of cell density. In some other embodiments, a clustering algorithm can be applied to segment the histology image. For instance, a k-means clustering algorithm can be applied to each histology image for segmentation of cell nuclei and anatomical features, such as prostate glands, present in normal regions. Other examples of segmentation include segmenting nuclei, cytoplasm, and extracellular fluid, or segmenting based on physical features of the cells, such as roundness and size.

By way of example, H&E stained brain specimens can be provided and segmented into histology tissue types, histological features, or both, and then co-registered manually to high-resolution medical images of the region best representing the histological landmarks. All other medical imaging contrasts can then be co-registered and resampled to match the high-resolution medical images.

Histology can then be resampled to the high-resolution medical image resolution for a direct one-to-one comparison. As one example, the cell count and average percentage of each histology component can be calculated within the space occupied by each medical image resolution voxel. Cell count can likewise be calculated as the sum of the cell counts within regions defined by each voxel. Histological segmentation values, along with the medical image values within each voxel, can then be extracted and combined across all specimens, as will now be described in more detail.

Figure 3:
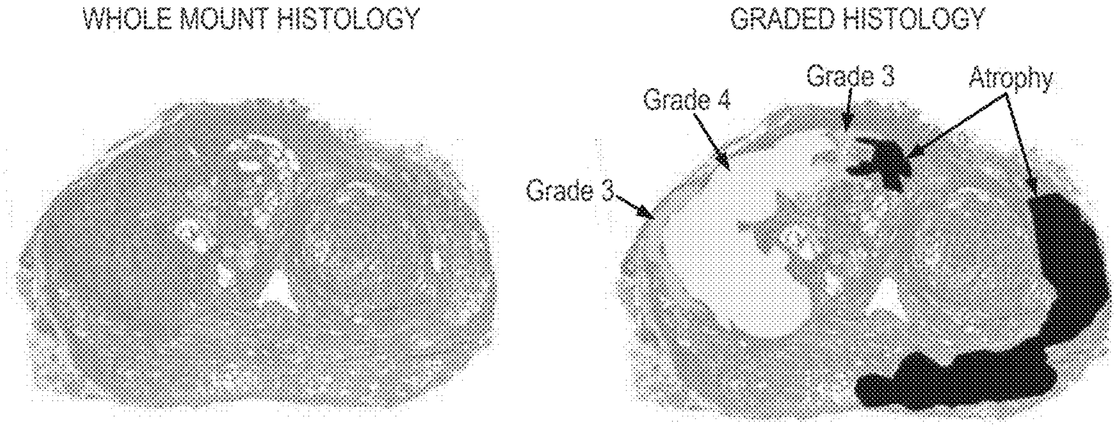
FIG. 3 is an example of a graded tissue sample indicating a scalar value, which in this case is a prostate Gleason score.

As another example, a prostate histology image can be manually scored for Gleason score, and the Gleason score can be computationally labeled and provided as a histological feature on a categorical scale rather than a continuous scale. An example of a whole mount histology image and the corresponding graded histology image is shown in FIG. 3.

Referring still to FIG. 1, an image contrast matrix, C, is formed based on the provided medical images, as indicated at step 106. Each row in this matrix is associated with one voxel location in the medical images and each column is associated with a different imaging contrast values for that voxel location. For example, the image contrast matrix can be an M×N matrix, where M is the total number of voxels in a two-dimensional image matrix associated with the acquired medical images, and N is the total number of different image contrasts represented by the medical images. As an example, the medical image data within a region sampled histologically can be represented by a 20×20 image matrix, resulting in M=400. In this example, if three different sets of images are obtained, each for a different image contrast, then N=3. For instance, the three different image contrasts may include $T_1$-weighting, contrast-enhanced $T_1$-weighting, and an ADC map.

In some instances, the histological features and the medical images may have a different spatial resolutions. In these instances, the histological features, medical images, or both can be resampled to the same resolution. As an example, the histological features can be down-sampled to the same spatial resolution as a medical image. The medical images of the tissue samples may also need to be co-registered with the histology images. In some instances, co-registration of the histology and clinically acquired images may be difficult because sometimes the histology and medical imaging slices will not line up. In these instances, the high-resolution medical images can be rotated or otherwise transformed using image processing to best line up the slices.

A histological feature matrix, H, is formed based on histological information obtained from the tissue sample, as indicated at step 108. Each row in this matrix is associated with one voxel location and each column is associated with a different histological feature computed at that voxel location. For example, the histological feature matrix can be an M×P matrix, where M is the total number of voxels in a two-dimensional image matrix associated with the acquired medical images, and P is the total number of different histological features represented in the histological feature matrix. As an example, M can be 400 and P can be one, where only the histological feature cell density is represented in the histological feature matrix. In this example, the histological feature matrix is a column vector associating spatial locations attributed to the voxel locations in the medical image matrix to cell density computed from a histological image or slide of the sample.

A machine learning algorithm is used to train a model that determines the relationship between the image contrast matrix, C, and the histological feature matrix, H, as indicated at step 110. As one example, the machine learning algorithm can be based on a partial least squares ("PLS") regression. In other examples, the machine learning algorithm can be based on a neural network, a support vector machine, a naïve Bayesian classifier, or linear discriminant analysis.

In general, a PLS regression builds a linear model predicting a set of dependent variables from a set of independent variables. This is accomplished using features from both principal component analysis and multiple linear regression, where predicted and observable variables are projected into a new space. In this instance, the dependent variables are the histological feature values and the independent variables are the image contrast values. The PLS regression determines the relationship between the image contrast matrix and the histological feature matrix, which constitute training data, to iteratively generate a mathematical model (i.e., the trained model). The trained model converges to a final form when it reduces the error (i.e., uncertainty) to a tolerable amount set by the user. The finalized model can then be used to predict values associated with a test dataset of medical images acquired for a particular subject.

Figure 4:
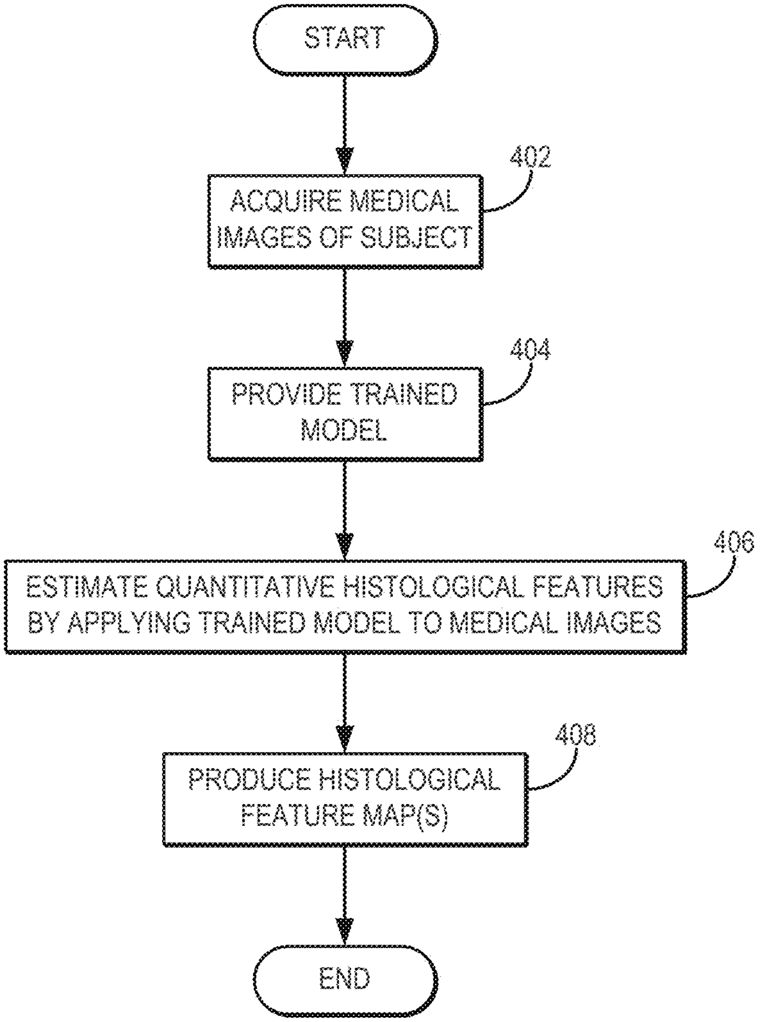
FIG. 4 is a flowchart setting forth the steps of an example method for estimating quantitative histological features based on medical images acquired from a subject using a trained model, such as the trained model generated according to the method of FIG. 1.

Referring now to FIG. 4, a flowchart is illustrated as setting forth the steps of an example method for producing a quantitative histological feature map based on medical images of a subject. The method includes acquiring image data from a subject using a medical imaging system, as indicated at step 402. As an example, the medical imaging system can be a magnetic resonance imaging ("MRI") system; an x-ray imaging system, including a computed tomography ("CT") system; an ultrasound imaging system; an optical imaging system; a nuclear medicine-based imaging system, such as a positron emission tomography ("PET") system; and so on.

After the one or more medical images of the subject have been acquired, the previously computed trained model is provided, as indicated at step 404. For instance, the trained model can be retrieved from data storage. In some instances, the provided trained model may include more imaging contrasts than have been acquired for a given subject or, similarly, may include more histological features than are desired to be estimated for a given subject or from a database of other subjects including imaging data and histological feature data. In either of these instances, the provided trained model can be trimmed to remove the additional imaging contrasts, or to remove the unwanted histological features.

The trained model is then applied to the one or more medical images to derive estimates of the quantitative histological features of the tissues depicted in the medical images, as indicated at step 406. For instance, the trained model is then applied to the medical images to determine on a voxel-wise basis what histological feature value best fits the combination of image contrasts in that voxel. This technique generates not only quantitative estimates of the histological features, but as indicated at step 408, also generates histological feature maps. For instance, the quantitative histological feature values can be assigned to voxel locations corresponding to the voxel locations in the respective medical images.

Figure 5A:
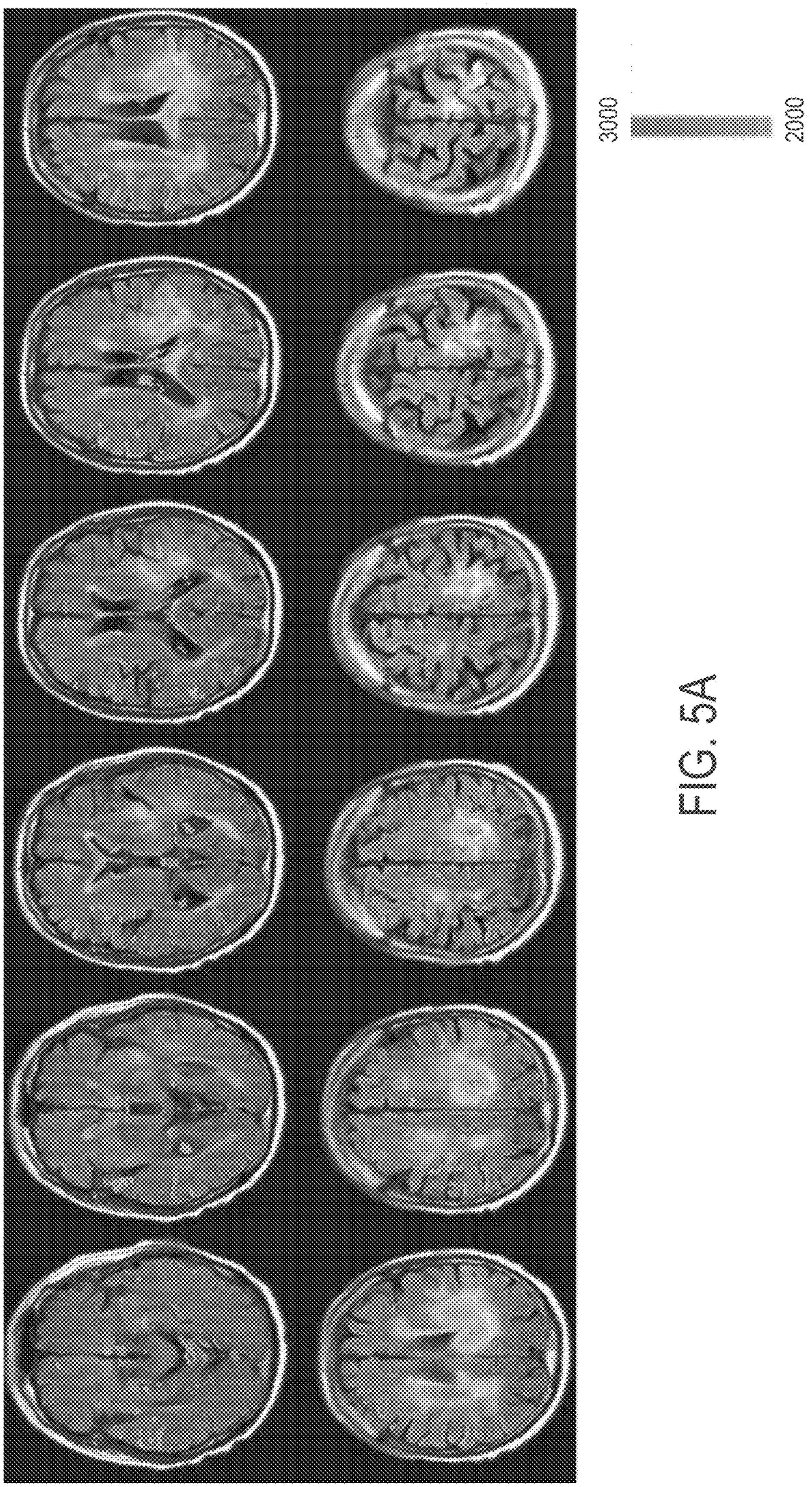
FIG. 5A illustrates an example of quantitative histological feature maps indicating cell density in a subject's brain.
Figure 5B:
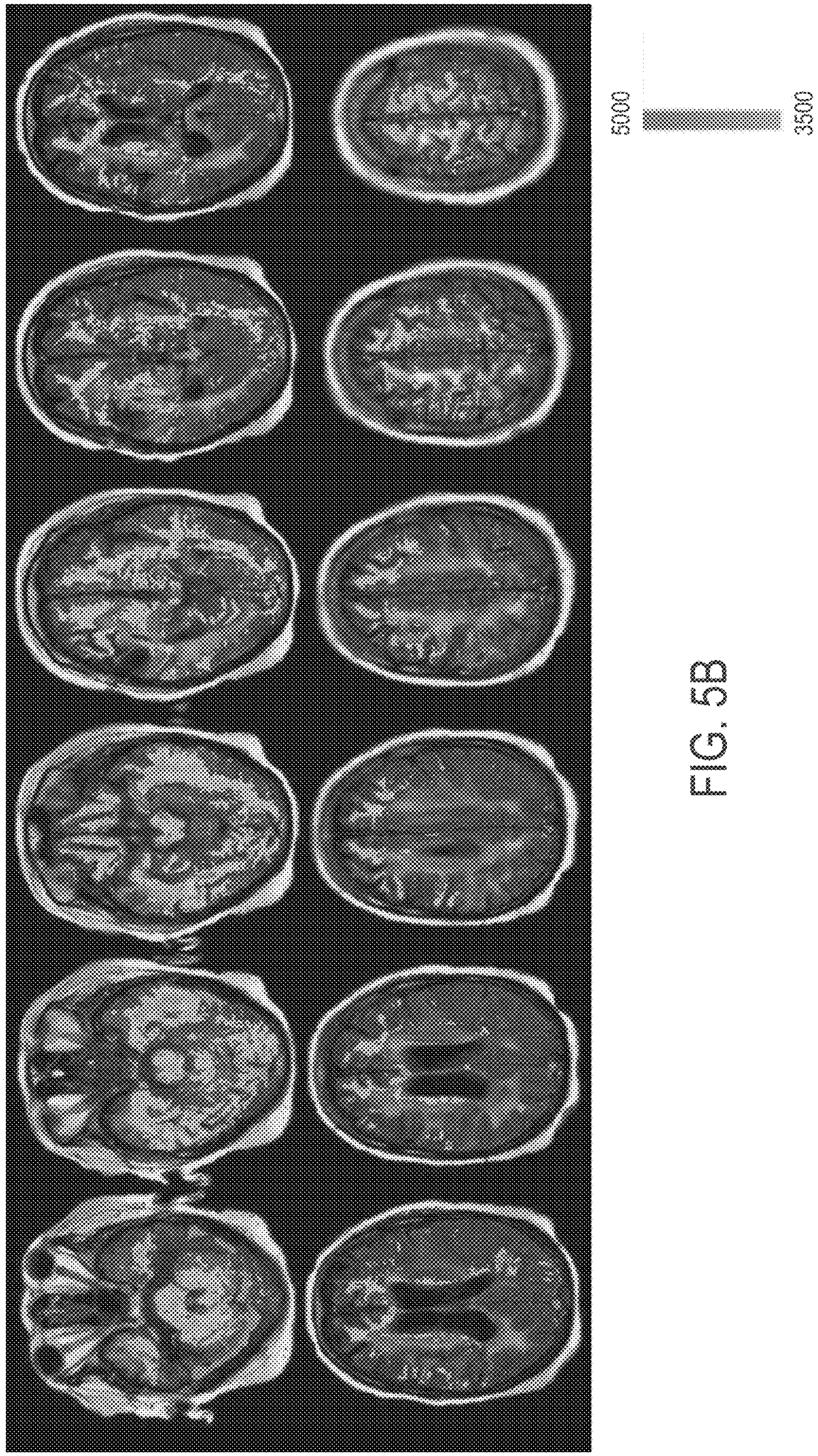
FIG. 5B illustrates another example of quantitative histological feature maps indicating cell density in a different subject's brain.
Figure 5C:
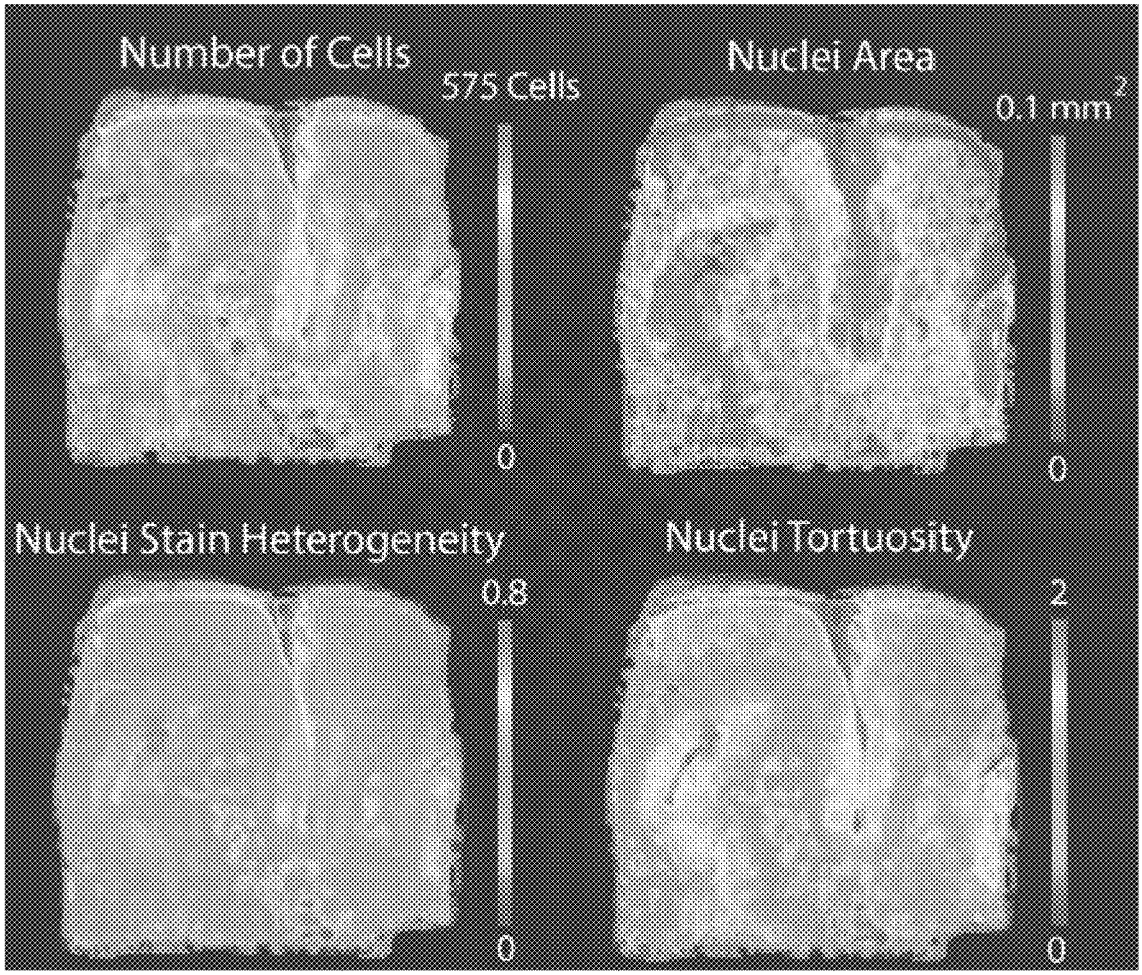
FIG. 5C illustrates example quantitative histological feature maps for brain tissue, including number of cells, nuclei area, nuclei stain heterogeneity, and nuclei tortuosity.

Examples of intensity thresholded histological feature maps for brain tissue are illustrated in FIGS. 5A-5I. Maps depicting cell density in two different subjects' brains are illustrated in FIG. 5A and FIG. 5B. In these examples, the cell density values are overlaid on anatomical images of the subjects. FIG. 5C illustrates four example histological feature maps for brain tissue. In this example, the histological features include number of cells, nuclei area, nuclei stain heterogeneity, and nuclei tortuosity.

Figure 5D:
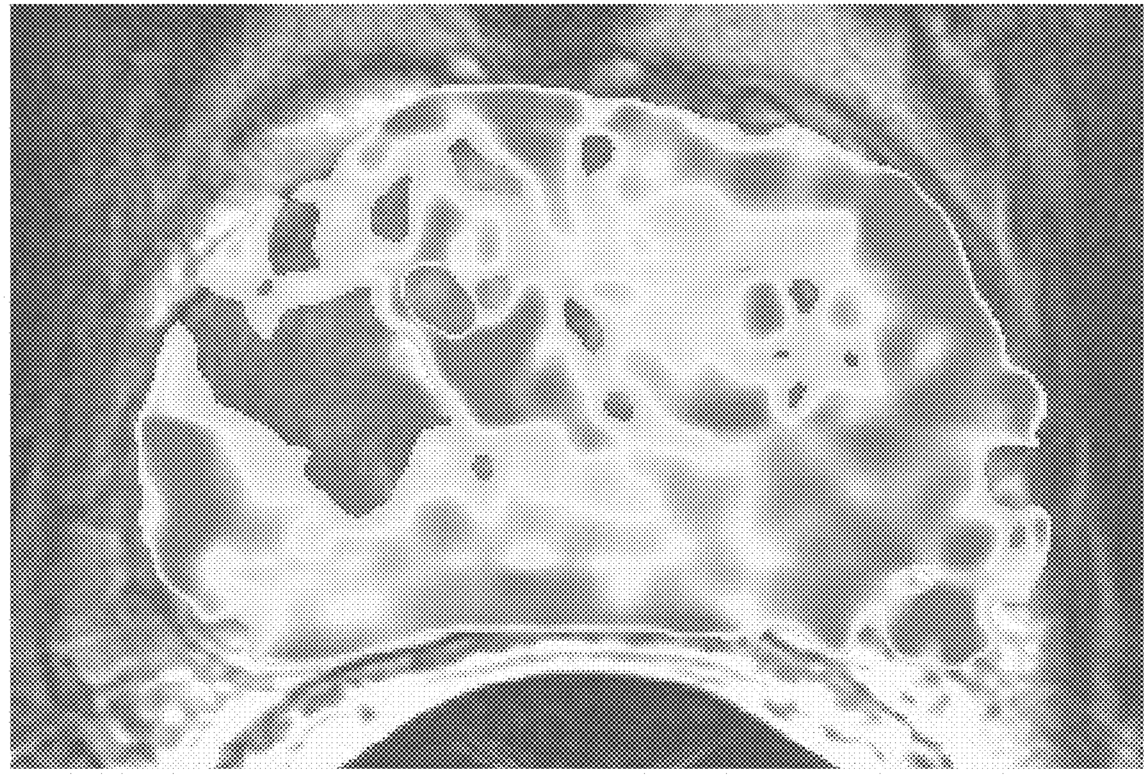
FIG. 5D is an example of a quantitative histological feature map of lumen density, which depicts lumen density values overlaid on an anatomical image of a prostate.
Figure 5E:
FIG. 5E is an example of a quantitative histological feature map of gland wall density, which depicts gland wall density values overlaid on an anatomical image of a prostate.
Figure 5F:
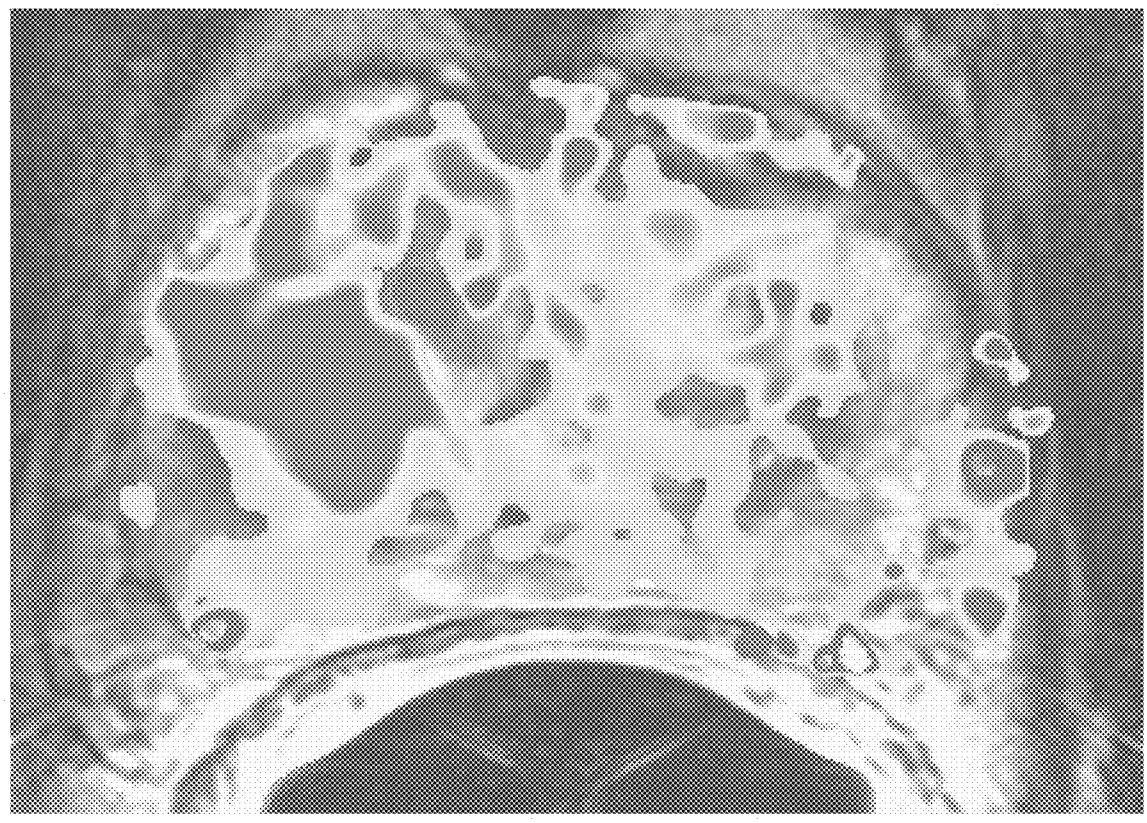
FIG. 5F is an example of a quantitative histological feature map depicting values indicating a ratio of gland wall density to lumen density overlaid on an anatomical image of a prostate.
Figure 5G:
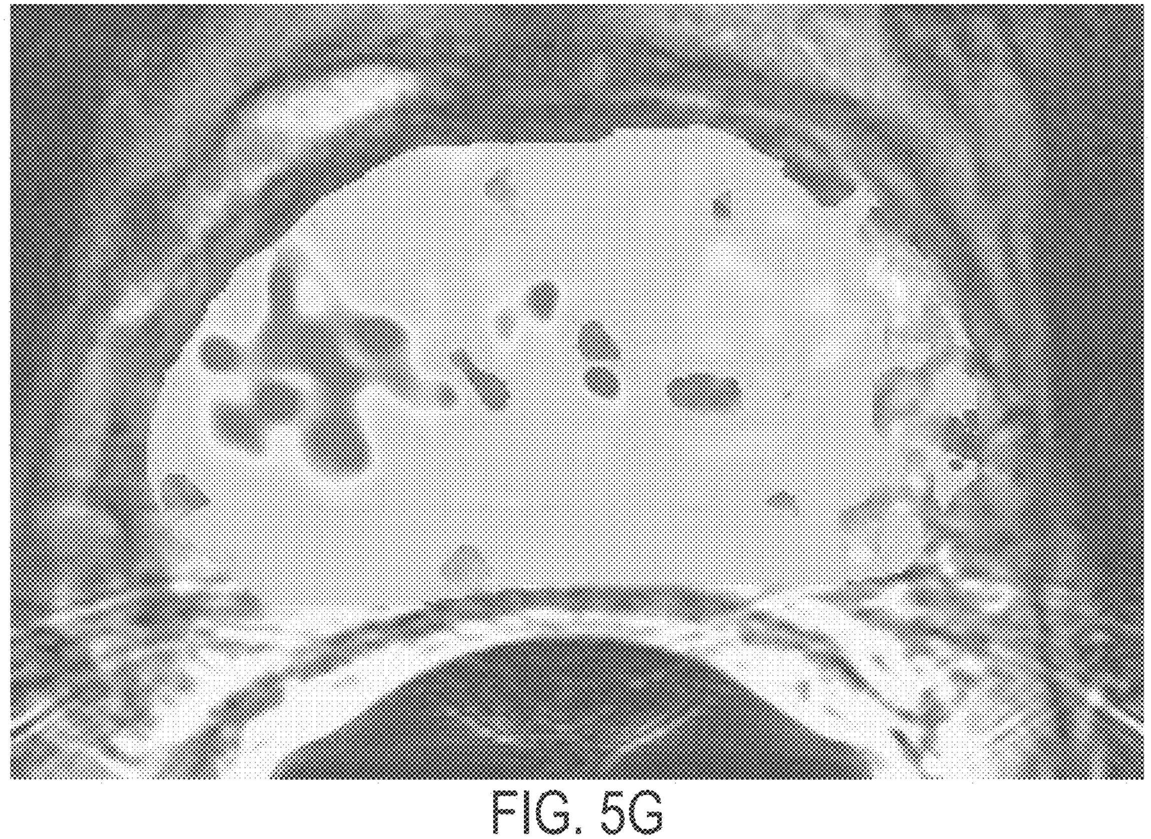
FIG. 5G is an example of a quantitative histological feature map of lumen tortuosity, which depicts lumen tortuosity values overlaid on an anatomical image of a prostate.
Figure 5H:
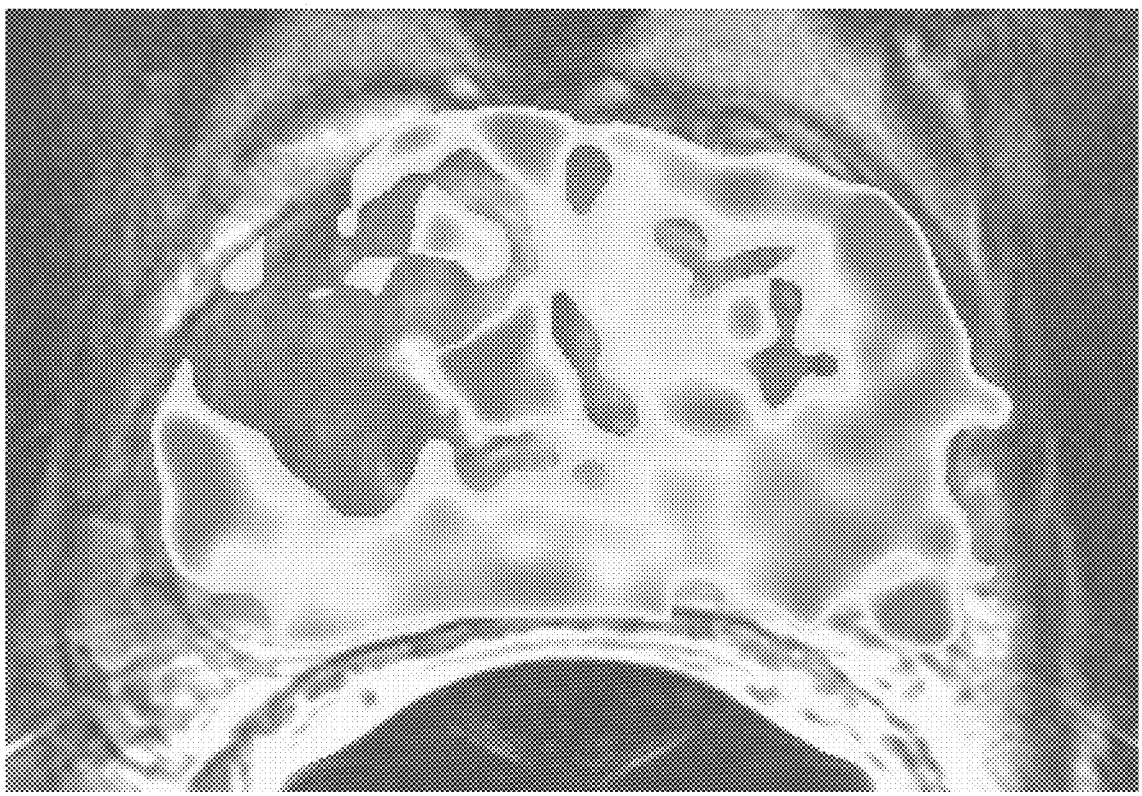
FIG. 5H is an example of a quantitative histological feature map of lumen size, which depicts lumen size values overlaid on an anatomical image of a prostate.
Figure 5I:
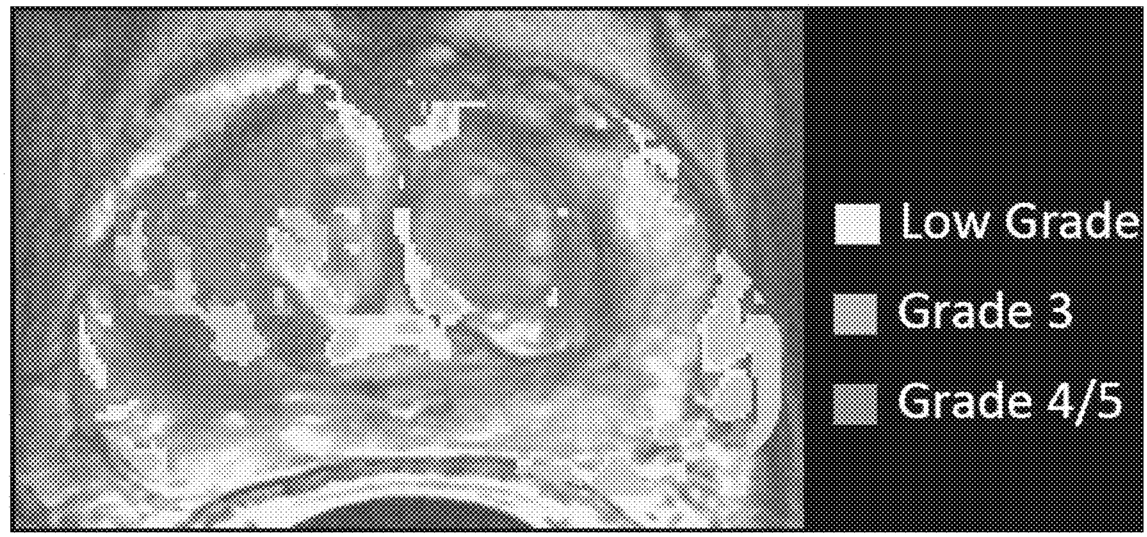
FIG. 5I is an example virtual Gleason score map depicting Gleason score values overlaid on an anatomical image of a prostate.

FIGS. 5D-5I illustrate example histological feature maps for prostate tissue in a particular subject. Specifically, FIG. 5D is a map of lumen density map, FIG. 5E is a gland wall density map, FIG. 5F is a map depicting a ratio of gland wall to lumen density, FIG. 5G is a lumen tortuosity map, FIG. 5H is a lumen size map, and FIG. 5I is a virtual Gleason score map.

The systems and methods of the present invention are thus capable of providing information about the microscopic factors that contribute to the appearance of brain tumors and other pathological tissue states by correlating medical images of ex vivo tissue samples, in vitro tissue samples, or in vivo tissue samples with the histological features derived from those samples. The trained model generated in this manner can then be used to extract quantitative information about histological features from medical images acquired from living subjects. As such, the systems and methods of the present invention provide clinically realizable quantitative imaging of histological features.

As one example of the clinical utility of the present invention, as mentioned above, in some embodiments parametric images, such as ADC maps, can be correlated with histological features in the trained model. ADC measures the average diffusion of water molecules within each voxel, and is generally heightened in the presence of vasogenic edema due to the increased levels of extracellular fluid. ADC, however, has been shown to decrease in the presence of hypercellularity. Some debate remains as to whether or not ADC is predictive of tumor grade, as some studies have found a correlation, while others have found considerable overlap between tumor grades, or no correlation at all. Because the systems and methods of the present invention can correlate multiple image contrasts to a single histological feature, a more reliable assessment of the correlation between ADC and cell density can be achieved when implementing the present invention.

Another example of the clinical utility of the present invention is in its ability to differentiate between different sources of contrast enhancement in medical images based on the underlying histological features. One particular example is being able to differentiate pseudo-progression from viable tumor. In general, pseudo-progression is the presence of contrast enhancement following radiation and chemotherapy that either recedes over time or remains stable. By using tissue samples that contain both enhancing tumor and enhancing radiation effects, the trained model can be trained to differentiate between these sources of contrast enhancement and other sources of contrast enhancement. For instance, the trained model can be designed to differentiate between radiation treatment effect from viable tumor. In these embodiments, a trained model can be generated and a leave-one-out ("LOO") approach can be used to optimize the included medical image contrasts using the percentage of necrosis within each voxel as the histological feature of interest. Based on the medical image characteristics, the generated trained model will be able to differentiate the two types of contrast enhancement.

In some embodiments, the systems and methods described here can be used to generate maps of histological features at medical imaging resolution by establishing the relationship between in vivo medical imaging and ex vivo microscopic histopathological metrics of interest. Precise histological validation and correlation with several medical imaging contrasts allows the unique possibility of generating a PLS trained model, similar to the methods discussed above, that can be applied to the entire imaging dataset. Because each voxel has a histological correlate, where some number of cancer cells and other histological features determine the resulting imaging contrasts, this dataset can be used to predict histological values in voxels not sampled with histology. In these embodiments, whole histological feature maps of a whole tissue volume can be generated using a trained model that is trained with a small sub-sample of actual tissue. For instance, a whole prostate histological feature map can be generated based on a trained model generated using only a small sub-sample of prostate tissue.

In these embodiments, a trained model is generated using all available histology specimens combined with corresponding matrices of imaging contrasts. Each row in the imaging array contains the values from each imaging contrast at each voxel sampled with histology. Each down-sampled histological feature then becomes the unexplained variable of interest. The trained model is then converged upon with all available histology and all available imaging contrasts. This model can then be applied to the whole tissue volume to determine the histological features in regions not sampled ex vivo. This technique, in effect, generates voxel-wise maps of whatever histological feature is fed into the training algorithm.

Figure 6:
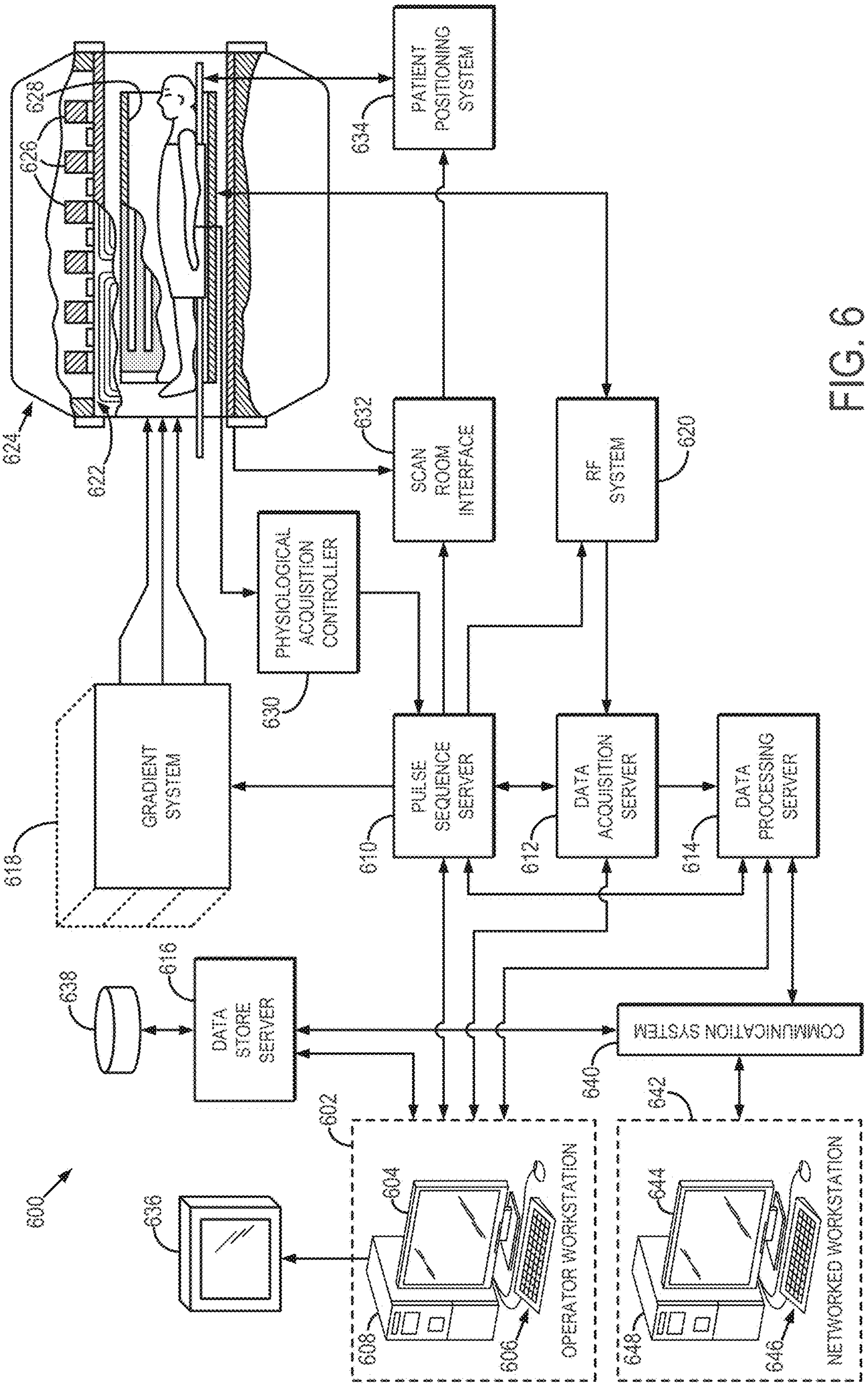
FIG. 6 is a block diagram of an example of a magnetic resonance imaging ("MRI") system.

Referring particularly now to FIG. 6, an example of a magnetic resonance imaging ("MRI") system 600 is illustrated. The MRI system 600 includes an operator workstation 602, which will typically include a display 604; one or more input devices 606, such as a keyboard and mouse; and a processor 608. The processor 608 may include a commercially available programmable machine running a commercially available operating system. The operator workstation 602 provides the operator interface that enables scan prescriptions to be entered into the MRI system 600. In general, the operator workstation 602 may be coupled to four servers: a pulse sequence server 610; a data acquisition server 612; a data processing server 614; and a data store server 616. The operator workstation 602 and each server 610, 612, 614, and 616 are connected to communicate with each other. For example, the servers 610, 612, 614, and 616 may be connected via a communication system 640, which may include any suitable network connection, whether wired, wireless, or a combination of both. As an example, the communication system 640 may include both proprietary or dedicated networks, as well as open networks, such as the internet.

The pulse sequence server 610 functions in response to instructions downloaded from the operator workstation 602 to operate a gradient system 618 and a radiofrequency ("RF") system 620. Gradient waveforms necessary to perform the prescribed scan are produced and applied to the gradient system 618, which excites gradient coils in an assembly 622 to produce the magnetic field gradients $G_x$, $G_y$, and $G_z$ used for position encoding magnetic resonance signals. The gradient coil assembly 622 forms part of a magnet assembly 624 that includes a polarizing magnet 626 and a whole-body RF coil 628.

RF waveforms are applied by the RF system 620 to the RF coil 628, or a separate local coil (not shown in FIG. 6), in order to perform the prescribed magnetic resonance pulse sequence. Responsive magnetic resonance signals detected by the RF coil 628, or a separate local coil (not shown in FIG. 6), are received by the RF system 620, where they are amplified, demodulated, filtered, and digitized under direction of commands produced by the pulse sequence server 610. The RF system 620 includes an RF transmitter for producing a wide variety of RF pulses used in MRI pulse sequences. The RF transmitter is responsive to the scan prescription and direction from the pulse sequence server 610 to produce RF pulses of the desired frequency, phase, and pulse amplitude waveform. The generated RF pulses may be applied to the whole-body RF coil 628 or to one or more local coils or coil arrays (not shown in FIG. 6).

The RF system 620 also includes one or more RF receiver channels. Each RF receiver channel includes an RF preamplifier that amplifies the magnetic resonance signal received by the coil 628 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2}; \tag{1}$$

and the phase of the received magnetic resonance signal may also be determined according to the following relationship:

$$\varphi = \tan^{-1}\left(\frac{Q}{I}\right). \tag{2}$$

The pulse sequence server 610 also optionally receives patient data from a physiological acquisition controller 630. By way of example, the physiological acquisition controller 630 may receive signals from a number of different sensors connected to the patient, such as electrocardiogramaignals from electrodes, or respiratory signals from a respiratory bellows or other respiratory monitoring device. Such signals are typically used by the pulse sequence server 610 to synchronize, or "gate," the performance of the scan with the subject's heart beat or respiration.

The pulse sequence server 610 also connects to a scan room interface circuit 632 that receives signals from various sensors associated with the condition of the patient and the magnet system. It is also through the scan room interface circuit 632 that a patient positioning system 634 receives commands to move the patient to desired positions during the scan.

The digitized magnetic resonance signal samples produced by the RF system 620 are received by the data acquisition server 612. The data acquisition server 612 operates in response to instructions downloaded from the operator workstation 602 to receive the real-time magnetic resonance data and provide buffer storage, such that no data is lost by data overrun. In some scans, the data acquisition server 612 does little more than pass the acquired magnetic resonance data to the data processor server 614. However, in scans that require information derived from acquired magnetic resonance data to control the further performance of the scan, the data acquisition server 612 is programmed to produce such information and convey it to the pulse sequence server 610. For example, during prescans, magnetic resonance data is acquired and used to calibrate the pulse sequence performed by the pulse sequence server 610. As another example, navigator signals may be acquired and used to adjust the operating parameters of the RF system 620 or the gradient system 618, or to control the view order in which k-space is sampled. In still another example, the data acquisition server 612 may also be employed to process magnetic resonance signals used to detect the arrival of a contrast agent in a magnetic resonance angiography ("MRA") scan. By way of example, the data acquisition server 612 acquires magnetic resonance data and processes it in real-time to produce information that is used to control the scan.

The data processing server 614 receives magnetic resonance data from the data acquisition server 612 and processes it in accordance with instructions downloaded from the operator workstation 602. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 614 are conveyed back to the operator workstation 602 where they are stored. Real-time images are stored in a data base memory cache (not shown in FIG. 6), from which they may be output to operator display 612 or a display 636 that is located near the magnet assembly 624 for use by attending physicians. Batch mode images or selected real time images are stored in a host database on disc storage 638. When such images have been reconstructed and transferred to storage, the data processing server 614 notifies the data store server 616 on the operator workstation 602. The operator workstation 602 may be used by an operator to archive the images, produce films, or send the images via a network to other facilities.

The MRI system 600 may also include one or more networked workstations 642. By way of example, a networked workstation 642 may include a display 644; one or more input devices 646, such as a keyboard and mouse; and a processor 648. The networked workstation 642 may be located within the same facility as the operator workstation 602, or in a different facility, such as a different healthcare institution or clinic.

The networked workstation 642, whether within the same facility or in a different facility as the operator workstation 602, may gain remote access to the data processing server 614 or data store server 616 via the communication system 640. Accordingly, multiple networked workstations 642 may have access to the data processing server 614 and the data store server 616. In this manner, magnetic resonance data, reconstructed images, or other data may be exchanged between the data processing server 614 or the data store server 616 and the networked workstations 642, such that the data or images may be remotely processed by a networked workstation 642. This data may be exchanged in any suitable format, such as in accordance with the transmission control protocol ("TCP"), the internet protocol ("IP"), or other known or suitable protocols.

Figure 7:
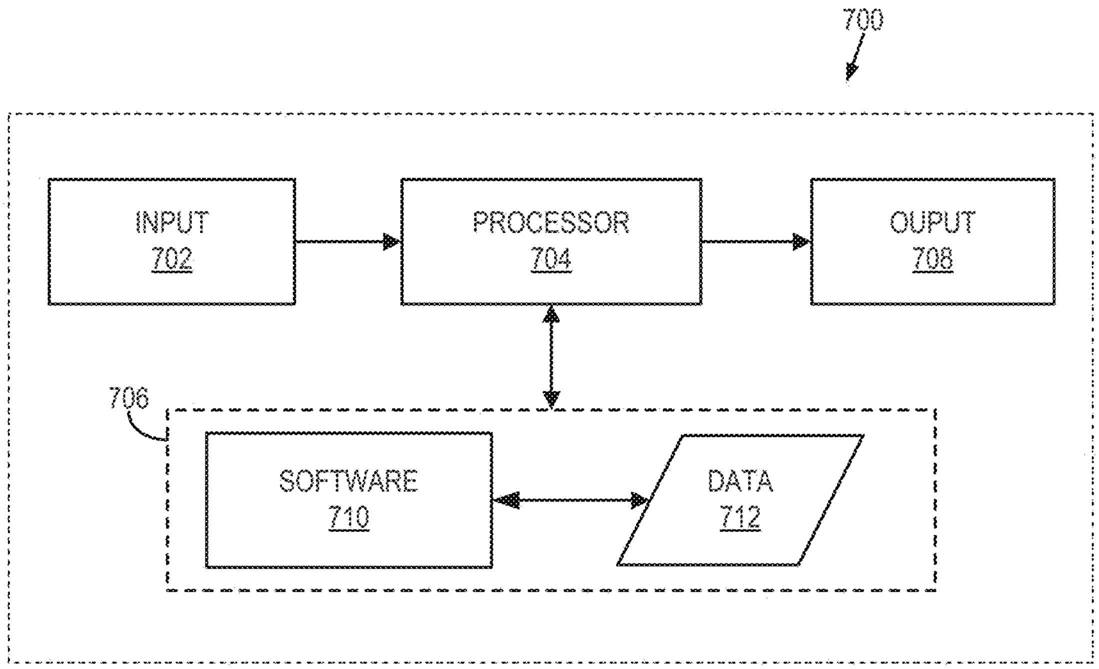
FIG. 7 is a block diagram of an example computer system than can be programmed or otherwise configured to implement the methods and algorithms described herein.

Referring now to FIG. 7, a block diagram is shown of an example computer system 700 for generating histological feature maps using an image-based histology-trained model, such as is described above in detail. The computer system 700 generally includes an input 702, at least one processor 704, a memory 706, and an output 708. The computer system 700 can also include any suitable device for reading computer-readable storage media. The computer system 700 may be, for example, a workstation, a notebook computer, a personal digital assistant ("PDA"), a multimedia device, a network server, a mainframe, or any other general-purpose or application-specific computing device. The computer system 700 may operate autonomously or semi-autonomously, or may read executable software instructions from the memory 706 or a computer-readable medium (e.g., a hard drive, a CD-ROM, flash memory), or may receive instructions via the input 702 from a user, or any another source logically connected to a computer or device, such as another networked computer or server. In general, the computer system 700 is programmed or otherwise configured to implement the methods and algorithms described above.

The input 702 may take any suitable shape or form, as desired, for operation of the computer system 700, including the ability for selecting, entering, or otherwise specifying parameters consistent with performing tasks, processing data, or operating the computer system 700. In some aspects, the input 702 may be configured to receive data, such as magnetic resonance images, histology images, or associated data. Such data may be processed as described above. In addition, the input 702 may also be configured to receive any other data or information considered useful for generating image-based histology-trained maps of histological features.

Among the processing tasks for operating the computer system 700, the at least one processor 704 may also be configured to receive data, such as magnetic resonance images, histology images, or associated data. In some configurations, the at least one processor 704 may also be configured to carry out any number of post-processing steps on data received by way of the input 702. In addition, the at least one processor 704 may be capable of generating histological feature maps as described above.

The memory 706 may contain software 710 and data 712, and may be configured for storage and retrieval of processed information, instructions, and data to be processed by the at least one processor 704. In some aspects, the software 710 may contain instructions directed to producing histological feature maps. Also, the data 712 may include any data necessary for operating the computer system 700, and may include any magnetic resonance images, histology images, or trained models as described above.

In addition, the output 708 may take any shape or form, as desired, and may be configured for displaying, in addition to other desired information, any histological feature maps.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for training a model with machine learning to differentiate between different sources of contrast enhancement in medical images, the steps of the method comprising:

providing to a computer system, a plurality of medical images, wherein the plurality of medical images comprises at least one medical image of each of a plurality of different tissue samples, wherein the plurality of different tissue samples contain both contrast-enhancing tumor and contrast-enhancing treatment effects;

providing to the computer system, quantitative histological feature values determined from the plurality of different tissue samples;

forming training data with the computer system, wherein the training data comprise an image contrast matrix formed from the plurality of medical images and a histological feature matrix formed from the quantitative histological feature values;

training a model on the training data using the computer system, wherein the model is trained on the training data using machine learning to differentiate between different sources of contrast enhancement based on a histological feature of interest; and storing the trained model with the computer system.

2. The method of claim 1, wherein the model is based on at least one of a neural network or a support vector machine.

3. The method of claim 1, wherein forming the training data comprises forming the histological feature matrix by resampling the quantitative histological feature values determined from the plurality of different tissue samples to a spatial resolution of the plurality of medical images.

4. The method of claim 1, wherein each row in the image contrast matrix is associated with one voxel location in the plurality of medical images and each column in the image contrast matrix is associated with a different imaging contrast value for each voxel location.

5. The method of claim 1, wherein each row in the histological feature matrix is associated with one voxel location and each column in the histological feature matrix is associated with a different one of the quantitative histological feature values computed at each voxel location.

6. The method of claim 1, wherein the histological feature of interest is a percentage of necrosis.

7. The method of claim 1, wherein the plurality of medical images comprises medical images acquired with at least one of a magnetic resonance imaging (MRI) system, an x-ray computed tomography (CT) system, an ultrasound imaging system, an optical imaging system, or a positron emission tomography (PET) system.

* * * * *